United States Patent [19]

Warriner

[11] Patent Number: Plant 5,340

[45] Date of Patent: Nov. 20, 1984

[54] ROSE PLANT JACTU

[75] Inventor: William A. Warriner, Tustin, Calif.

[73] Assignee: Jackson & Perkins Company, Medford, Oreg.

[21] Appl. No.: 475,162

[22] Filed: Mar. 14, 1983

[51] Int. Cl. ..... A01H 5/00

[52] U.S. Cl. ..... Plt./11

[58] Field of Search ..... Plt./11

*Primary Examiner*—Robert E. Bagwill

*Attorney, Agent, or Firm*—Klarquist, Sparkman, Campbell, Leigh & Whinston

[57] ABSTRACT

A hybrid tea rose variety having vigorous, free blooming bush, petal color which blends from near white to pink and red upon exposure to sunlight, large double flowers containing 55–60 petals, and little or no fragrance.

1 Drawing Figure

This present invention relates to a new and distinct variety of rose plant of the hybrid tea class which was originated by me by crossing the variety Love with the variety Color Magic.

The primary objective of this breeding was to produce a new rose variety combining the bud or flower of Love with the photosensitive characteristic of the flower pigment of variety Color Magic on a vigorous bush. This objective was substantially achieved along with other desirable improvements as evidenced by the following unique combination of characteristics which are outstanding in the new variety and which distinguish it from its parents, as well as from all other varieties of which I am aware:

1. Vigorous upright, free blooming bush.
2. Blend of colors from near white on unexposed petals to pink and red, R.H.S. 53C, after exposure to sunlight.
3. Large, very double flowers containing 55 to 60 petals.
4. Little or no fragrance.

Asexual reproduction of this new variety by budding, as performed at Wasco, Calif., shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color in terminology in accordance with The Royal Horticultural Society Colour Chart except where ordinary dictionary significance of color is indicated.

Parentge:

*Seed parent.*—Love.

*Pollen parent.*—Color Magic.

Classification:

*Botanical.*—Rosa hybrid.

*Commercial.*—Hybrid tea.

FLOWER

Observations made from specimens grown at Irvine, Calif. in November.

Blooming habit: Continuous.

Bud:

*Size.*—1⅛ To 1¼" when petals start to unfurl.

*Form.*—Pointed ovoid.

*Color.*—When sepals first divide outer surface of outside petals is Red 53C. When half blown; upper side of petals' color develops, upon exposure to sunlight, through Red 54 D, C and B to 53C in irregular areas, all colors being present at one time. Center of flower, receiving less sunlight, remains white at this stage. Color on lower side of petals is very similar to upper side except less area develops the deepest shade, Red 53C.

*Sepals.*—Color: Outer surface generally Green 138A with some overlay of Grayed Purple 183B. A few stipitate glands are borne on outer surface and edges of sepals. Three appendaged sepals lightly appendaged. Two unappendaged sepals hairy edged.

*Receptacle.*—Color: Green 138A. Shape: Funnel. Size: Large. Surface: Smooth.

*Peduncle.*—Length: Medium. Surface: Prickly. Color: Bronzy, near Grayed Purple 183B. Strength: Stiff, erect, heavy.

*Opening.*—Petals slightly curled causing a spiral type bud formation. Center petals often remain, covering reproductive parts.

Bloom:

*Size.*—Large. Averge open size: 5–5½".

*Borne.*—Singly, occasionally several together.

*Stems.*—Long.

*Form.*—When first open, high center. Permanence: Retains its form to the end.

*Petalage.*—Number of petals under normal conditions: 55–60.

*Color.*—Center of flower: Upper side of petals near Yellow 11C when freshly opened; color deepens first at petal tips when first exposed to sunlight through Red Group 54D, C, B and 53C. Reverse side of petals near Yellow 11C until exposed to sunlight and developing a color near Red Group 54D. Base of petals Yellow 12B at point of attachment. General tonality from a distance: Blend of near white to Yellow 11C and reds of Group 53 and 54.

*Variegations.*—As noted.

*Discoloration.*—General tonality at end of first day: Slight development of red color pigments. Third day: Color deepens on petal tips to mostly Red 53C, but center of flower usually remains near white.

*Fragrance.*—None.

Petals:

*Texture.*—Thin.

*Shape.*—Round.

*Form.*—Edges slightly quilled.

*Arrangement.*—Imbricated. Petaloids in center, few.

*Persistence.*—Drop off cleanly.

*Lastingness.*—On the plant, long. As cut flower, long.

PLANT

Form: Bush.

Growth: Very vigorous, upright.

Foliage: Number of leaflets on normal mid-stem leaves: 5 or 7.

*Size.*—Large.

*Quantity.*—Normal.

*Color.*—New foliage: Grayed Purple 183A. Old foliage: Green 131A.

Leaflets:

*Shape.*—Oval.

*Texture.*—Upper side: Leathery.

*Edge.*—Serrated.

*Serration.*—Single, small.

*Petiole.*—Rachis: Color: Reddish. Underside: Prickles.

*Stipules.*—Long, bearded.

*Disease resistance.*—Moderately resistant to mildew under normal growing conditions at Irvine, Calif.

Wood:

*New wood.*—Color: Reddish. Bark: Smooth.

*Old wood.*—Color: Green. Bark: Smooth.

Prickles:

*Quantity.*—On main stalks from base; ordinary. On laterals from stalk, ordinary.

*Form.*—Long, hooked downward.

*Color when young.*—Brown.

*Position.*—Irregular.

Small Prickles:

*Quantity.*—On main stalks, none. On laterals, none.

I claim:

1. A new and distinct variety of rose plant of the hybrid tea class, substantially as herein shown and described, characterized particularly as to novelty by the unique combination of its floriferous, upright plant, blend of flower color from white to red upon exposure to sunlight, large double flowers of little or no fragrance.

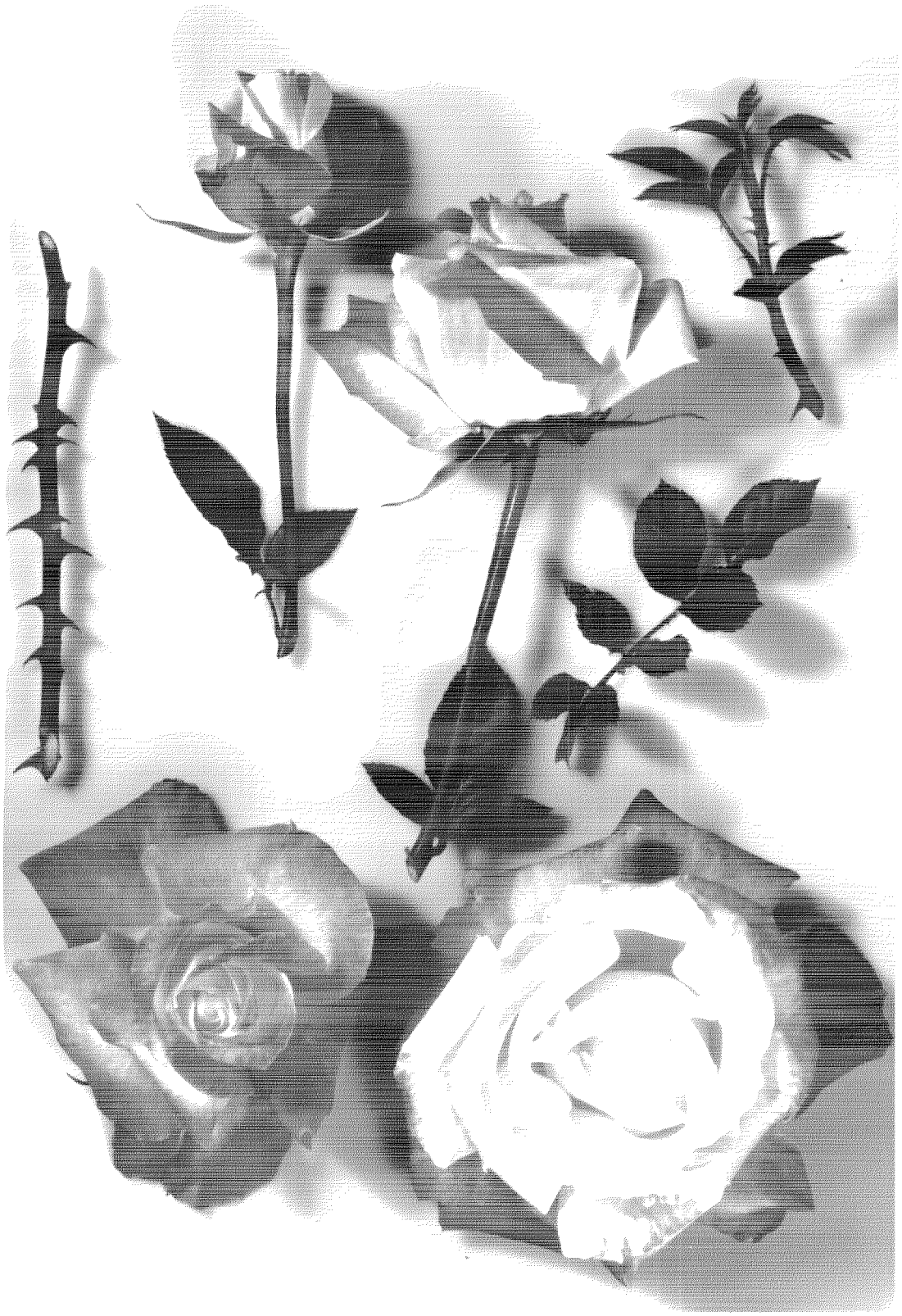

* * * * *